United States Patent
Dijkstra et al.

(10) Patent No.: US 9,066,926 B2
(45) Date of Patent: Jun. 30, 2015

(54) METHOD OF REDUCING EXERCISE-INDUCED JOINT PAIN IN NON-ARTHRITIC MAMMALS

(71) Applicant: Interhealth Nutraceuticals, Inc., Benicia, CA (US)

(72) Inventors: Paul Dijkstra, San Francisco, CA (US); Francis C. Lau, Benicia, CA (US); James Lugo, Benicia, CA (US); Zainulabedin M. Saiyed, San Ramon, CA (US)

(73) Assignee: Interhealth Nutraceuticals, Inc., Benicia, CA (US)

( * ) Notice: Subject to any disclaimer, the term of this patent is extended or adjusted under 35 U.S.C. 154(b) by 0 days.

(21) Appl. No.: 14/153,841

(22) Filed: Jan. 13, 2014

(65) Prior Publication Data

US 2015/0119335 A1  Apr. 30, 2015

Related U.S. Application Data

(60) Provisional application No. 61/895,332, filed on Oct. 24, 2013.

(51) Int. Cl.
  *A61K 38/00* (2006.01)
  *A61K 38/39* (2006.01)
  *A61K 38/16* (2006.01)

(52) U.S. Cl.
  CPC *A61K 38/39* (2013.01); *A61K 38/16* (2013.01)

(58) Field of Classification Search
  None
  See application file for complete search history.

(56) References Cited

U.S. PATENT DOCUMENTS

| | | | |
|---|---|---|---|
| 5,399,347 | A | 3/1995 | Trentham et al. |
| 5,529,786 | A | 6/1996 | Moore |
| 5,570,144 | A | 10/1996 | Lofgren-Nisser |
| 5,637,321 | A | 6/1997 | Moore |
| 5,645,851 | A | 7/1997 | Moore |
| 6,162,787 | A | 12/2000 | Sorgente et al. |
| 6,372,794 | B1 | 4/2002 | Nimni |
| 7,083,820 | B2 | 8/2006 | Schilling et al. |
| 2002/0086070 | A1 | 7/2002 | Kuhrts |
| 2006/0062859 | A1 | 3/2006 | Blum et al. |
| 2007/0293427 | A1 | 12/2007 | Vouland et al. |
| 2010/0215731 | A1 | 8/2010 | Emans et al. |
| 2011/0218151 | A1 | 9/2011 | Opheim |
| 2012/0294898 | A1 | 11/2012 | Hubbard et al. |

FOREIGN PATENT DOCUMENTS

| | | |
|---|---|---|
| CN | 101822684 A | 9/2010 |
| CN | 102423487 A | 4/2012 |
| CN | 103203012 A | 7/2013 |
| JP | 2003048850 A | 2/2003 |

OTHER PUBLICATIONS

MedlinePlus, Cartilage Disorders, Jan. 5, 2012, download online on Jul. 22, 2014 form URL: <http://www.nlm.nih.gov/medlineplus/cartilagedisorders.html>.*

NHS Choices, Cartilage damage, Jan. 15, 2012, download online on Jul. 22, 2014 form URL: <http://www.nhs.uk/Conditions/Cartilage-damage/Pages/Introduction.aspx>.*

Shek PN and Shephard RJ: Physical exercise as a human model of limited inflammatory response., *Can J Physiol Pharmacol* (1998) 76:589-597.

Kiviranta I, Tammi M, Jurvelin J, et al.: Articular cartilage thickness and glycosaminoglycan distribution in the canine knee joint after strenuous running exercise, *Clin Orthop Relat Res* (1992) 302-308.

Guilak F: Biomechanical factors in osteoarthritis, *Best Pract Res Clin Rheumatol* (2011) 25:815-823.

Kawamura S, Lotito K, and Rodeo SA: Biomechanics and healing response of the meniscus, *Oper Tech Sports Med* (2003) 11:68-76.

Ramage L, Nuki G, and Salter DM: Signalling cascades in mechanotransduction: Cell-matrix interactions and mechanical loading, *Scand J Med Sci Sports* (2009) 19:457-69.

Honda K, Ohno S, Tanimoto K, et al.: The effects of high magnitude cyclic tensile load on cartilage matrix metabolism in cultured chondrocytes, *Eur J Cell Biol* (2000) 79:601-9.

Agarwal S, Deschner J, Long P, et al.: Role of NF-kappab transcription factors in antiinflammatory and proinflammatory actions of mechanical signals, *Arthritis Rheum* (2004) 50:3541-3548.

Berg V, Sveinbjornsson B, Bendiksen S, et al.: Human articular chondrocytes express chemR23 and chemerin; chemR23 promotes inflammatory signalling upon binding the ligand chemerin (21-157), *Arthritis Res Ther* (2010) 12:R228.

Millward-Sadler SJ, Wright MO, Lee H, et al.: Integrin-regulated secretion of interleukin 4: A novel pathway of mechanotransduction in human articular chondrocytes, *J Cell Biol* (1999) 145:183-189.

Millward-Sadler SJ, Wright MO, Davies LW, et al.: Mechanotransduction via integrins and interleukin-4 results in altered aggrecan and matrix metalloproteinase 3 gene expression in normal, but not osteoarthritic, human articular chondrocytes. *Arthritis Rheum* (2000) 43:2091-2099.

Doi H, Nishida K, Yorimitsu M, et al.: Interleukin-4 downregulates the cyclic tensile stress-induced matrix metalloproteinases-13 and cathepsin b expression by rat normal chondrocytes, *Acta Med Okayama* (2008) 62:119-126.

Yorimitsu M, Nishida K, Shimizu A, et al.: Intra-articular injection of interleukin-4 decreases nitric oxide production by chondrocytes and ameliorates subsequent destruction of cartilage in instability-induced osteoarthritis in rat knee joints, *Osteoarthritis Cartilage* (2008) 16:764-771.

van Meegeren ME, Roosendaal G, Jansen NW, et al.: IL-4 alone and in combination with IL-10 protects against blood-induced cartilage damage. *Osteoarthritis Cartilage* (2012) 20:764-72.

(Continued)

*Primary Examiner* — Karlheinz R Skowronek
*Assistant Examiner* — Sergio Coffa
(74) *Attorney, Agent, or Firm* — Marshall, Gerstein & Borun LLP

(57) ABSTRACT

The present invention relates to a method of treating exercise-induced joint pain in arthritis-free mammals by the administration of undenatured Type II collagen.

16 Claims, 3 Drawing Sheets

(56) References Cited

OTHER PUBLICATIONS

Pufe T, Lemke A, Kurz B, et al.: Mechanical overload induces VEGF in cartilage discs via hypoxia-inducible factor. *Am J Pathol* (2004) 164:185-192.

Ostrowski K, Rohde T, Asp S, et al.: Pro- and anti-inflammatory cytokine balance in strenuous exercise in humans, *J Physiol* (1999) 515 (Pt 1 ):287-91.

Allen JL, Cooke ME, and Alliston T: ECM stiffness primes the TGFbeta pathway to promote chondrocyte differentiation. *Mol Biol Cell* (2012) 23:3731-3742.

Bougault C, Aubert-Foucher E, Paumier A, et al.: Dynamic compression of chondrocyte-agarose constructs reveals new candidate mechanosensitive genes. *PLoS One* (2012) 7:e36964.

Li TF, O'Keefe RJ, and Chen D: TGF-beta signaling in chondrocytes, *Front Biosci* (2005) 10:681-688.

Donovan J and Slingerland J: Transforming growth factor-beta and breast cancer: Cell cycle arrest by transforming growth factor-beta and its disruption in cancer, *Breast Cancer Res* (2000), 2:116-24.

Rosier RN, O'Keefe RJ, Crabb ID, et al.: Transforming growth factor beta: An autocrine regulator of chondrocytes, *Connect Tissue Res* (1989) 20:295-301.

Roman-Blas JA, Stokes DG, and Jimenez SA: Modulation of TGF-beta signaling by proinflammatory cytokines in articular chondrocytes, *steoarthritis Cartilage* (2007) 15:1367-1377.

Loeser RF: Aging and osteoarthritis: The role of chondrocyte senescence and aging changes in the cartilage matrix, *Osteoarthritis Cartilage* (2009) 17:971-979.

van Beuningen HM, van der Kraan PM, Arntz OJ, et al.: Protection from interleukin 1 induced destruction of articular cartilage by transforming growth factor beta: tudies in anatomically intact cartilage in vitro and in vivo, *Ann Rheum Dis* (1993) 52:185-191.

Bagchi D, Misner B, Bagchi M, et al.: Effects of orally administered undenatured type II collagen against arthritic inflammatory diseases: A mechanistic exploration, *Int J Clin Pharmacol Res* (2002) 22:101-110.

Trentham DE, Dynesius-Trentham RA, Orav EJ, et al.: Effects of oral administration of type II collagen on rheumatoid arthritis, *Science* (1993) 261 :1727-1730.

Crowley DC, Lau FC, Sharma P, et al.: Safety and efficacy of undenatured type II collagen in the treatment of osteoarthritis of the knee: A clinical trial, *Int J Med Sci* (2009) 6:312-321.

Tong T, Zhao W, Wu YQ, et al.: Chicken type II collagen induced immune balance of main subtype of helper T cells in mesenteric lymph node lymphocytes in rats with collagen-induced arthritis, *Inflamm Res* (2010) 59:369-377.

Nagler-Anderson C, Bober LA, Robinson ME, et al.: Suppression of type II collagen-induced arthritis by intragastric administration of soluble type II collagen. *Proc Natl Acad Sci U S A* (1986) 83:7443-7446.

Brandtzaeg P: 'ABC' of mucosal immunology, *Nestle Nutr Workshop Ser Pediatr Program* (2009) 64:23-38; discussion 38-43, 251-7.

Weiner HL, da Cunha AP, Quintana F, et al.: Oral tolerance. *Immunol Rev* (2011) 241:241-259.

Aletaha D, Neogi T, Silman AJ, et al.: 2010 rheumatoid arthritis classification criteria: An american college of rheumatology/european league against rheumatism collaborative initiative, *Arthritis Rheum* (2010) 62:2569-2581.

Altman R, Asch E, Bloch D, et al.: Development of criteria for the classification and reporting of osteoarthritis. Classification of osteoarthritis of the knee. Diagnostic and therapeutic criteria committee of the american rheumatism association, *Arthritis Rheum* (1986) 29:1039-1049.

Likert R: A technique for the measurement of attitudes, *Arch Psychol* (1932) 22:1-55.

Roos EM, Roos HP, Ekdahl C, et al.: Knee injury and osteoarthritis outcome score (KOOS)—validation of a swedish version, *Scand J Med Sci Sports* (1998) 8:439-448.

Lorig K, Stewart A, Ritter P, et al.: Outcome measures for health education and other health care interventions. Outcome measures for health education and other health care interventions, *Thousand Oaks, CA: SAGE Publications, Inc*. (1996). (Title Page, Copyright Page and Table of Contents).

Hawkey C, Laine L, Simon T, et al.: Comparison of the effect of rofecoxib (a cyclooxygenase 2 inhibitor), ibuprofen, and placebo on the gastroduodenal mucosa of patients with osteoarthritis: A randomized, double-blind, placebo-29 controlled trial. The rofecoxib osteoarthritis endoscopy multinational study group, *Arthritis Rheum* (2000) 43:370-377.

Pincus T, Koch GG, Sokka T, et al.: A randomized, double-blind, rossover clinical trial of diclofenac plus misoprostol versus acetaminophen in patients with osteoarthritis of the hip or knee, *Arthritis Rheum* (2001) 44:1587-1598.

Petrella RJ, DiSilvestro MD, and Hildebrand C: Effects of hyaluronate sodium on pain and physical functioning in osteoarthritis of the knee: A randomized, double-blind, placebo-controlled clinical trial, *Arch Intern Med* (2002) 162:292-298.

Enright PL and Sherrill DL: Reference equations for the six-minute walk in healthy adults, *Am J Respir Crit Care Med* (1998) 158:1384-1387.

Perry J: Gait analysis: Normal and pathological function, *Thorofare: SLACK Inc*. (1992). (Title Page, Copyright Page and Table of Contents).

Viera AJ: Predisease: When does it make sense? *Epidemiol Rev* (2011) 33:122-134.

Norkin CC and Levangie PK: Joint structure & function: a comprehensive analysis Philadelphia: F.A. Davis; (1992). (Title Page, Copyright Page and Table of Contents).

Shah N: Increasing knee range of motion using a unique sustained method, *N Am J Sports Phys Ther* (2008) 3:110-113.

Shelbourne KD, Biggs A, and Gray T: Deconditioned knee: The effectiveness of a rehabilitation program that restores normal knee motion to improve symptoms and function, *N Am J Sports Phys Ther* (2007) 2:81-89.

Serrao PR, Gramani-Say K, Lessi GC, et al.: Knee extensor torque of men with early degrees of osteoarthritis is associated with pain, stiffness and function, *Rev Bras Fisioter* (2012) 16:289-294.

Heiden TL, Lloyd DG, and Ackland TR: Knee extension and flexion weakness in people with knee osteoarthritis: Is antagonist cocontraction a factor? *J Orthop Sports Phys Ther* (2009) 39:807-815.

Karantanas AH, Magnetic resonance imaging findings in early osteoarthritis of the knee, in Touch Brief. (2007) p. 37-40.

Park MJ, Park KS, Park KK, et al.: A distinct tolerogenic subset of splenic IDO(+)CD11b(+) dendritic cells from orally tolerized mice is responsible for induction of systemic immune tolerance and suppression of collagen-induced arthritis, *Cell Immunol* (2012) 278:45-54.

Li MO and Flavell RA: TGF-beta: A master of all T cell trades, *Cell* (2008) 134:392-404.

Coombes JL, Siddiqui KR, Arancibia-Carcamo CV, et al.: A functionally specialized population of mucosal CD103+ dcs induces Foxp3+ regulatory t cells via a TGF-beta and retinoic acid-dependent mechanism, *J Exp Med* (2007) 204:1757-1764.

Ilan Y, Zigmond E, Lalazar G, et al.: Oral administration of OKT3 monoclonal antibody to human subjects induces a dose-dependent immunologic effect in T cells and dendritic cells, *J Clin Immunol* (2010) 30:167-77.

Caminiti L, Passalacqua G, Barberi S, et al.: A new protocol for specific oral tolerance induction in children with ige-mediated cow's milk allergy, *Allergy Asthma Proc* (2009) 30:443-8.

Ben Ahmed M, Belhadj Hmida N, Moes N, et al.: IL-15 renders conventional lymphocytes resistant to suppressive functions of regulatory T cells through activation of the phosphatidylinositol 3-kinase pathway, *J Immunol* (2009) 182:6763-70.

Courtenay JS, Dallman MJ, Dayan AD, et al.: Immunisation against heterologous type II collagen induces arthritis in mice, *Nature* (1980) 283:666-8.

Pelletier JP, Martel-Pelletier J, and Abramson SB: Osteoarthritis, an inflammatory disease: Potential implication for the selection of new therapeutic targets, *Arthritis Rheum* (2001) 44:1237-47.

Di Cesare Mannelli L, Micheli L, Zanardelli M, et al.: Low dose native type II collagen prevents pain in a rat osteoarthritis model, *BMC Musculoskelet Disord* (2013) 14:228.

(56) References Cited

OTHER PUBLICATIONS

Muller RD, John T, Kohl B, et al.: IL-10 overexpression differentially affects cartilage matrix gene expression in response to TNF-alpha in human articular chondrocytes in vitro, *Cytokine* (2008) 44:377-85.

Zouali M: Immunological tolerance: Mechanisms. eLS: John Wiley & Sons, Ltd; (2001).

Chu CR, Williams AA, Coyle CH, et al.: Early diagnosis to enable early treatment of pre-osteoarthritis. *Arthritis Res Ther* (2012) 14:212.

Marone PA, Lau FC, Gupta RC, et al.: Safety and toxicological evaluation of undenatured type ii collagen, *Toxicol Mech Methods* (2010) 20:175-89.

International Search Report and Written Opinion in corresponding PCT/US2014/11303 dated May 6, 2014.

International Search Report in Singapore Patent Application No. 11201403524R dated Feb. 11, 2015.

Written Opinion in Singapore Patent Application No. 11201403524R dated Mar. 20, 2015.

* cited by examiner

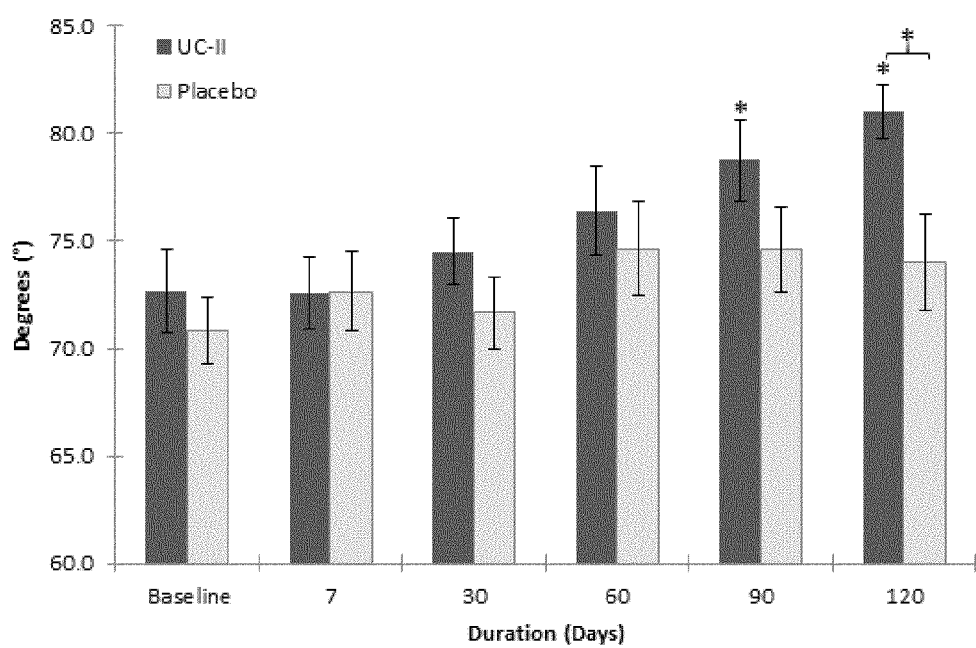
Figure 1. Average knee extension

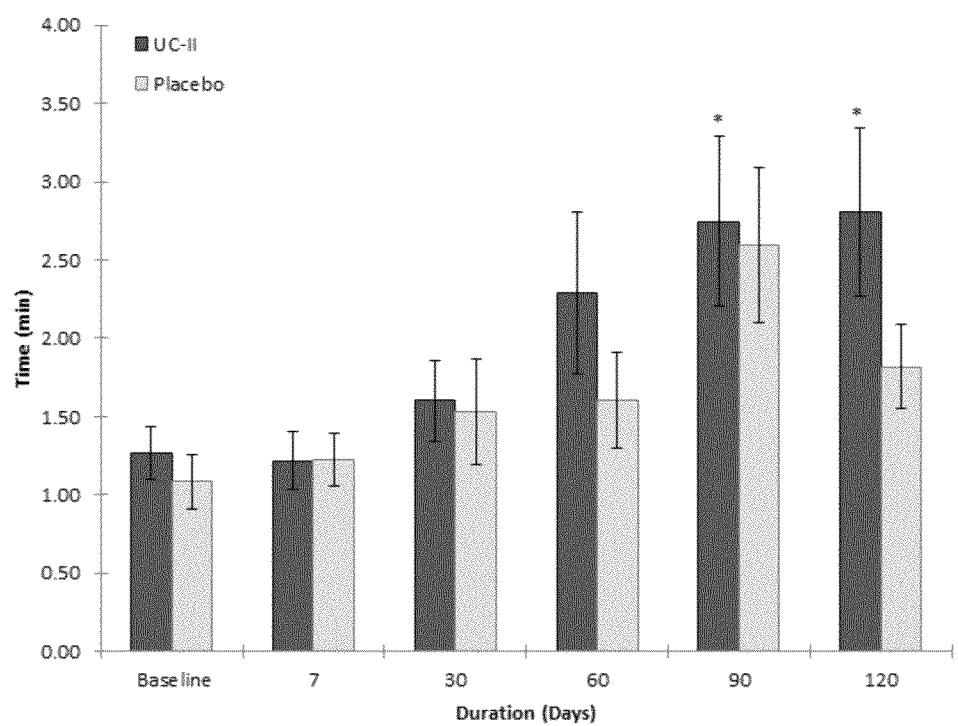
Figure 2. Time to onset of initial joint pain

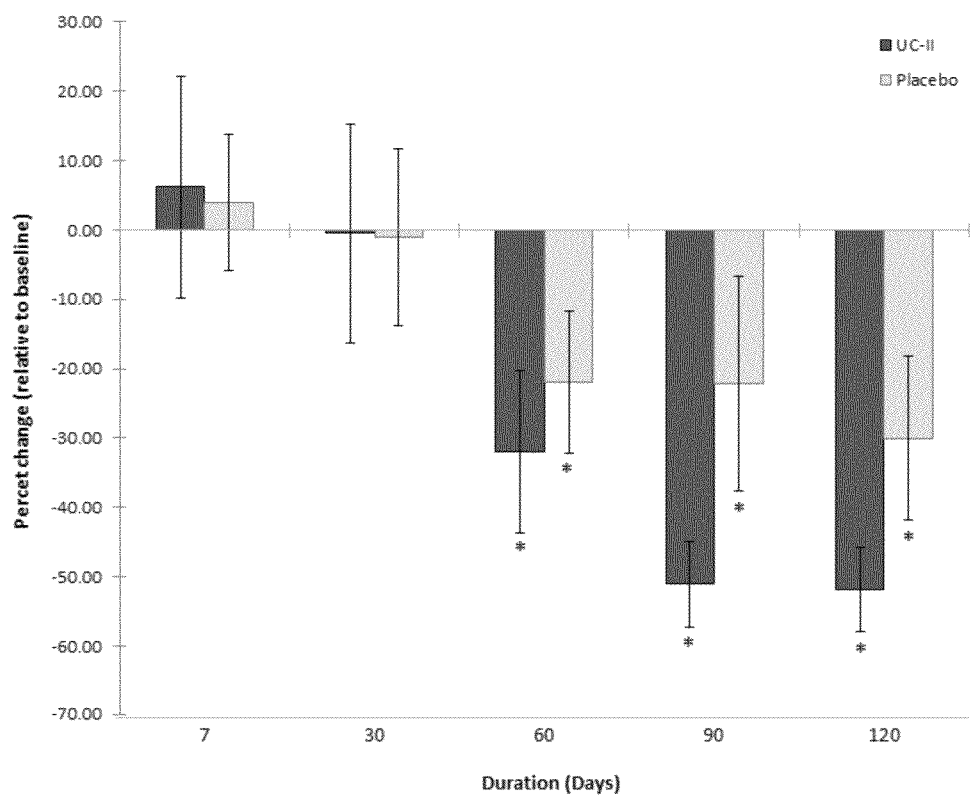
Figure 3. Percent change in time to complete recovery from joint pain

METHOD OF REDUCING EXERCISE-INDUCED JOINT PAIN IN NON-ARTHRITIC MAMMALS

CROSS-REFERENCE TO RELATED APPLICATIONS

This application is based on U.S. Provisional Application Ser. No. 61/895,332, filed Oct. 24, 2013.

BACKGROUND OF THE INVENTION

The present invention is directed to treating joint pain and joint mobility in non-arthritic mammalian subjects.

Of interest to the present invention is the disclosure of Trentham, U.S. Pat. No. 5,399,347 which is directed to a method of treating autoimmune arthritis by the oral, enteral or by-inhalation administration of collagen protein or the biologically active peptide fragments thereof. In particular, Trentham teaches that administration of collagen is effective in treating autoimmune arthritis by means of oral antigen tolerization therapy. According to these methods collagen and biologically active peptides are administered to suppress the autoimmune response responsible for arthritis while leaving other immune functions of the treated mammal intact.

Previous studies have shown that small doses of undenatured Type II collagen modulate joint health in both OA and RA [24-26]. Tong et al. [27] have shown, using an in vivo model of collagen induced arthritis (CIA), that ingesting microgram quantities of undenatured type II collagen significantly reduces circulating levels of inflammatory cytokines thereby decreasing both the incidence and the severity of arthritis similar to results obtained by others [28]. The ability to alter immunity via the ingestion of a food, or an antigen is called oral tolerance. This is an ongoing normal physiological process that protects the alimentary tract against untoward immunological damage [29, 30]. Research into its mechanism of action has revealed that several distinct types of T regulator cells mediate this phenomenon by releasing IL-10 and TGF-$\beta$ [30]. It has also been shown that this effect is transitory in nature requiring that the food, or antigen, be consumed continuously in order to maintain the tolerogenic state [30].

Also of further interest to the present application are the disclosures of Moore U.S. Pat. Nos. 5,570,144, 5,529,786, 5,637,321 and 5,645,851 which are directed to the administration of type II collagen for the treatment of Rheumatoid Arthritis and Osteoarthritis. It has further been observed that undenatured type II collagen maintaining the native conformation of its proteins is particularly useful in treating arthritis.

While both rheumatoid and osteoarthritis are inflammatory conditions not all joint pain is associated with an inflammatory condition. Such pain is frequently induced by exercise or other mechanical stressors and there remains a desire for therapies capable of preventing and treating such pain in humans and other mammals.

SUMMARY OF THE INVENTION

The present invention relates to the discovery that the administration of undenatured Type II collagen is effective in treating exercise-induced joint pain in arthritis-free mammals. Specifically, the invention provides methods of treating exercise-induced joint pain in arthritis-free mammals comprising administering undenatured Type II collagen in an amount effective to reduce such exercise-induced joint pain.

As used herein "arthritis free mammals" are mammals which are free of the clinical signs of arthritis. Arthritis free humans are defined as those who present with either no or an insufficient number of diagnosable markers to classify as arthritic, as outlined by the American College of Rheumatology (ACR) guidelines Aletaha D, Neogi T, Silman A J, et al.: 2010 rheumatoid arthritis classification criteria: An American college of rheumatology/European league against rheumatism collaborative initiative. Arthritis Rheum 2010, 62:2569-81 and Altman R, Asch E, Bloch D, et al.: Development of criteria for the classification and reporting of osteoarthritis. Classification of osteoarthritis of the knee. Diagnostic and therapeutic criteria committee of the American rheumatism association. Arthritis Rheum 1986, 29:1039-49.

Not only does administration of undenatured Type II collagen serve to reduce joint pain during strenuous exercise in arthritis-free subjects but it has also been found that the administration of undenatured Type II collagen is effective in lengthening the period of strenuous exercise in an arthritis-free mammal before joint pain is experienced. Further, the invention provides methods of speeding recovery from exercise-induced joint pain in arthritis-free mammals comprising administering undenatured Type II collagen in an amount effective to speed the recovery from exercise-induced joint pain.

The method of the invention is particularly useful in treating exercise induced knee pain which can be evidenced not only by subjective measurements of pain but also by improvements in range of motion including knee joint flexion and knee joint extension.

More generally, the methods of the invention are directed to treating joint pain in an arthritis-free mammal which is due to a mechanical stressor. While strenuous exercise is one such stressor, other stressors which apply mechanical force to a joint can also induce pain in the absence of arthritis. Such stressors thus include acute injury and physical trauma to a joint such as through an accident. The invention thus contemplates treating joint pain resulting from such stressors.

While the methods of the invention are particularly effective in reducing exercise-induced knee pain in arthritis-free humans it is believed that the administration of undenatured Type II collagen will reduce exercise-induced pain in other joints and will be effective in reducing exercise induced pain on other non-arthritic mammals such as dogs and horses.

The undenatured Type II collagen is preferably administered in oral form but it is contemplated that other enteral modes of administration would be particularly effective. A particularly preferred mode of administration is as a capsule but undenatured Type II collagen may also be readily incorporated into beverages, foods and dietary supplements. Thus, the undenatured Type II collagen may be consumed in the form of a dosage form selected from the group consisting of capsules, tablets, gummy chewables, edible films, lozenges, and powders. Suitable capsules can be solid or liquid filled and suitable tablets can include those which are sublingual, chewable, effervescent, extended release and enteric coated. The undenatured Type II collagen may also be consumed as a beverage and in a syrup or liquid suspension and can also be consumed in the form of an edible supplement. While non-enteral modes of administration are contemplated they would generally not be preferred.

Undenatured Type II collagen may be administered according to the invention in dosages of from 0.1 mg or less up to 5000 mg or more per day with a preferred human dosage ranges being from 1 mg to 200 mg per day with dosages of 5 mg to 40 mg per day being more preferred. It is well within the ordinary skill in the art to empirically determine preferred dosages of undenatured Type II collagen according to the species and size of mammalian subject as well as the severity of non-arthritic pain suffered by the subject.

BRIEF DESCRIPTION OF THE FIGURES

FIG. 1 depicts knee extension as measured by goniometry. Values are presented as Mean±SEM. *p≤0.05 indicates a statistically significant difference versus baseline or placebo. Number of completers: n=24 in undenatured Type II collagen group (n=3 dropouts); n=20 in placebo group (n=6 dropouts; n=2 did not participate in ROM assessment);

FIG. 2 depicts impact of stepmill procedure on the onset of pain. Values are presented as Mean±SEM. *p≤0.05 indicates a statistically significant difference from baseline. Number of completers: n=19 in undenatured Type II collagen group (n=3 dropouts; n=5 did not have pain); n=20 in placebo group (n=6 dropouts; n=1 did not have pain; n=1 did not use stepmill); and FIG. 3 depicts percent change in time to complete recovery from pain. Values are presented as Mean±SEM. *p≤0.05 indicates a statistically significant difference from baseline. Number of completers: n=18 in undenatured Type II collagen group (n=3 dropouts; n=5 did not have pain; n=1 time to complete recovery from pain was not achieved); n=20 in placebo group (n=6 dropouts; n=1 did not have pain; n=1 did not use stepmill).

DETAILED DESCRIPTION

The present invention is directed to the observation that the administration of undenatured Type II collagen is not only useful in the treatment of joint pain for subjects suffering from autoimmune arthritis and inflammatory arthritis conditions such as rheumatoid arthritis and osteo arthritis but is also particularly effective in treating exercise induced joint pain in mammals not suffering from arthritis. The present invention thus relates to the discovery that the administration of undenatured Type II collagen is effective in treating exercise-induced joint pain in arthritis-free mammals. Specifically, the invention provides methods of treating exercise-induced joint pain in arthritis-free mammals comprising administering undenatured Type II collagen in an amount effective to reduce such exercise-induced joint pain. Not only does administration of undenatured Type II collagen serve to reduce joint pain during strenuous exercise in arthritis-free subjects but it has also been found that the administration of undenatured Type II collagen is effective in lengthening the period of strenuous exercise in an arthritis-free mammal before joint pain is experienced. The administration of Type II collagen also serves to speed recovery from exercise-induced joint pain in arthritis-free mammals. These results are surprising in light of the absence of any autoimmune condition and in light of the fact that exercise-induced joint pain has generally been considered to be the result of a physical stressor rather than an inflammatory process such as rheumatoid or osteo arthritis.

Nevertheless, the impact of strenuous exercise on knee joints presents with many of the features of inflammatory disease including localized pain and stiffness [1]. It has been shown that when dogs undergo a strenuous running regimen significant losses in articular cartilage and glycosaminoglycans occur [2]. Such studies suggest that strenuous exercise may activate some of the same physiological processes that occur in arthritic disease [2-4]. In fact, in vitro studies have shown that many of the cytokines implicated in the onset and progression of both rheumatoid arthritis (RA) and osteoarthritis (OA) also appear to regulate the remodeling of the normal knee extracellular matrix (ECM) following strenuous exertion [5].

When normal chondrocytes undergo strenuous mechanical stimulation, under static conditions, their physiology shifts towards ECM breakdown as indicated by the upregulation of several metalloproteinases (MMPs), including MMP-13, as well as tumor necrosis factor (TNF)-α, interleukin (IL)-1β, IL-6, and various aggrecanases [5, 6]. This in vitro catabolic response is mediated by changes in the phosphorylation, the expression, or the translocation of several transcription factors to the cell nucleus including NF-κB, p38 MAPK, Akt, and ERK [7, 8]. By contrast, normal chondrocytes produce the anti-inflammatory cytokine IL-4 when mechanically stimulated under moderate and dynamic conditions [9]. The secretion of this autocrine molecule not only helps in shifting chondrocyte metabolism towards the synthesis of aggrecan and type II collagen but it also downregulates production of nitric oxide (NO) and various MMPs and aggrecanases [10-12]. This conclusion is corroborated by the finding that pretreatment of strenuously compressed normal chondrocytes with IL-4 attenuates 5 their catabolic response [11]. This suggests that IL-4 plays a key role in downregulating remodeling functions, restoring articular cartilage homeostasis, as well as decreasing chondrocyte apoptosis following strenuous mechanical loading [12, 13].

Mechanically stressed chondrocytes also produce a number of other molecules known to participate in inflammatory responses [14]. They include prostaglandin $E_2$, NO, and vascular endothelial growth factor. These are proinflammatory molecules that, in conjunction with TNF-α, IL-6 and IL-1β, result in a localized, and transitory, inflammatory-like response that is part of the normal repair process occurring in knee joints, and serves to moderate remodeling events [3]. Ostrowski et al. [15] have shown that healthy individuals express up to 27-fold greater concentrations of the anti-inflammatory cytokine IL-10 in blood following a marathon run when compared to IL-10 blood levels at rest. This finding is not surprising given that these same individuals also show marked increases in the proinflammatory cytokines TNF-α, IL-1β, and IL-6. It therefore appears that in healthy subjects undergoing strenuous exertion, the induction of proinflammatory cytokines is offset by the synthesis of anti-inflammatory agents as part of the recovery process. This view is supported by the observation that IL-10 reduces the catabolic impact of IL-1β and TNFα on cartilage explants from healthy volunteers, and this effect is enhanced by combining IL-10 with IL-4 [13].

Another protein released by dynamically compressed chondrocytes is transforming growth factor (TGF)-β [16-18]. This factor is secreted by many cell types and is known to interfere with the cell cycle and arrest differentiation [19].

With regard to chondrocytes, TGF-β induces cell proliferation in vitro and slows terminal differentiation into hypertrophic cells [20]. Numerous studies have shown that TGF-β reverses the in vitro catabolic effect of various proinflammatory cytokines on normal chondrocytes as well as chondrocytes harvested from RA and OA donors [21-23].

The methods of the present invention utilize the administration of undenatured Type II collagen which can be derived from a variety of mammalian sources with avian sources being particularly preferred. The animal tissue used in the practice of this invention is can be warm or cold blooded and can be derived from fish such as salmon and shark. Nevertheless poultry cartilage preferably chicken cartilage as obtained from chicken less than about one year of age is a particularly useful source of undenatured Type II collagen, although other warm-blooded animal tissue containing Type II collagen, such as turkey cartilage, bovine cartilage and the vitreous humor of eyes, may be employed if desired.

Of interest to the present application is the disclosure of Schilling U.S. Pat. No. 7,083,820 which discloses preferred methods for producing undenatured Type II collagen. A particularly preferred undenatured Type II collagen is available commercially as UC-II® from InterHealth Nutraceuticals, Benicia, Calif. UC-II is a natural ingredient which contains a glycosylated, undenatured type-II collagen [24].

In preparing the poultry or warm-blooded animal tissue for oral administration the Type II collagen containing tissue is first dissected free of surrounding tissues and diced or otherwise comminuted by means known in the art desirably into particles no larger than a dose. The particulated cartilage is sterilized by means which do not affect or denature the structure of a major portion of the Type II collagen in the tissue and formed into doses containing therapeutically effective levels of undenatured Type II collagen, said levels being generally in the amount of at least about 0.01 gram and preferably from about 0.1 to about 0.5 grams of animal tissue in a dose. Being a natural product some variation from sample to sample is to be expected. These variations can be minimized by blending after comminution. The blending can be aided by analytical techniques that are known in the art which allow the measurement of the amount of undenatured Type II collagen and other antigens.

These measurements will allow blending of batches to obtain uniformity and in some cases to modify potency by increasing certain antigen levels by mixing cartilage from different sources. The optimum dosage may vary and is readily determined by means known in the art. The effective use of a broader range of undenatured Type II collagen containing animal tissue is surprising in view of the prior art which has utilized principally only chicks of less than three weeks of age to depolymerize, extract the water-soluble portion and then highly purify the Type II procollagen. The usefulness of the more mature chickens allows an almost 100 fold increase in the amount of harvestable undenatured Type II collagen from a single animal. This, of course, makes the desired product more readily available in therapeutic quantities, and also greatly decreases the possibility of microcontamination due to the reduced handling during separation from relatively few animals.

A critical step in the preparation of undenatured Type II collagen is the sterilization of the animal tissue either before or after comminution, thus it is essential that a sterilization procedure is employed which maintains the water insoluble structure of the Type II collagen in the animal tissue and also does not involve the denaturization of the Type II collagen in the animal tissue. Treating the animal tissue at elevated temperatures with water, such as exposing the tissue to boiling water substantially decreases the effectiveness of the animal tissue by causing the Type II collagen to become denatured. The treatment with acid causes the Type II collagen to become depolymerized into the less desirable water-soluble Type II procollagen. Preferred methods of sterilizing the comminuted tissue includes washing the comminuted Type II collagen with an oxidizing agent such as hydrogen peroxide or sodium hypochlorite. Exposure to radiation is also a desirable means of sterilizing the Type II collagen.

The amount of undenatured Type II collagen in a dose consumed at any given time will vary with the purpose of the consumption, the severity of symptoms, as well as the condition, age, weight, medical history and general physical characteristics of the patient to be treated. Consequently the doses, the frequency and time period over which the doses are administered will vary widely. It is not necessary for a single dose to contain an effective dose, although that is of course preferred, if multiple doses can be administered. The undenatured Type II collagen dose of the present invention may be extended by combination with other digestible ingredients such as in the form of aqueous dispersions, such as milk, or in combination with other proteinaceous substances, sugars, and starches. It may advantageously be administered directly as a comminuted solid as in an encapsulated comminuted solid, as a compression formed pill, as well as a slurry with or without other digestible compositions such as, for example, foodstuffs. It may be packaged in a sterile manner or sterilized after packaging and may be stored at room temperature or reduced temperature. Alternately it may be stored at sub-freezing temperature to prevent spoilage and may be frozen with other food substances in concentrated form.

Example 1

According to this example a randomized, double-blind, placebo-controlled study was conducted in healthy subjects who had no prior history of arthritic disease or joint pain at rest but experienced joint discomfort with physical activity.

Methods

UC-II® brand undenatured Type II collagen is derived from chicken sternum. For the clinical study, 40 mg of UC-II® brand undenatured Type II collagen material (Lot 1109006), which provides 10.4±1.3 mg of native type-II collagen, was encapsulated in an opaque capsule with excipients. Placebo was dispensed in an identical capsule containing only excipients (microcrystalline cellulose, magnesium stearate and silicon dioxide). Both study materials were prepared in a good manufacturing practice (GMP)-certified facility and provided by InterHealth Nutraceuticals, Inc. (Benicia, Calif.). Subjects were instructed to take one capsule daily with water before bedtime.

Recruitment of Subjects

One hundred and six subjects were screened for eligibility using the inclusion-exclusion criteria defined in Table 1. Only healthy adults who presented with no knee joint pain at rest and no diagnosable markers indicative of active arthritic disease, as outlined by the American College of Rheumatology (ACR) guidelines [31, 32], were admitted into the study. To accomplish this, all potential subjects were screened for the ACR specified clinical symptoms by a board certified physician and completed a medical history. Subjects presenting with any knee pain at rest and at least 3 of 6 clinical classification criteria, which included age greater than 50 years, morning stiffness in the knee joint lasting 30 minutes or less, crepitus on knee joint manipulation, body tenderness, bony enlargements, knee swelling or presence of excess fluid, and palpable warmth, were excluded. Potential subjects reporting the occasional use of NSAIDs, other pain relief medication, or anti-inflammatory supplements underwent a 2-week washout period before randomization.

TABLE 1

Inclusion-Exclusion Criteria

Inclusion

Subject must be ≥30 and ≤65 years of age
Body mass index (BMI) must be ≥18 and 35 kg/m$^2$
Knee joint criteria: (1) no knee joint discomfort at rest; (2) must achieve a knee joint discomfort score of at least 5 on an 11-point Likert scale within 10 minutes of initiating the stepmill protocol
Maintain existing food and physical activity patterns throughout the study period
Judged by Investigator to be in general good health on the basis of medical history
Subject understands the study procedures and provides signed informed consent to participate in the study and authorizes the release of relevant health information to the study investigator
Females must agree to use approved birth control methods during the study

Exclusion

Subjects with any indicators of arthritis, joint disorders, or history of immune system or autoimmune disorders
Daily use of NSAIDs; however, daily use of 81 mg of aspirin for cardioprotection is allowed
Daily use of anti-inflammatory or omega-3-fatty acid dietary supplements or using supplements to maintain joint health 30 days prior to screening
Subjects with a history of knee or hip joint replacement surgery, or any hip or back pain which interferes with ambulation
Use of any immunosuppressive drugs in the last 12 months (including steroids or biologics)
Glucocorticoid injection or hyaluronic acid injection in affected knee within 3 months prior to enrollment
History of surgery or significant injury to the target joint within 6 months prior to study enrollment, or an anticipated need for surgical or invasive procedure that will be performed during the study
Subjects with a chronic pain syndrome and in the judgment of the Investigator is unlikely to respond to any therapy
Participation in a clinical study with exposure to any non-registered drug product within 30 days prior
Subjects who have any physical disability which could interfere with their ability to perform the functional performance measures included in this protocol
Any significant GI condition that would potentially interfere with the evaluation of the study product
Clinically significant renal, hepatic, endocrine (including diabetes mellitus), cardiac, pulmonary, pancreatic, neurologic, hematologic, or biliary disorder
Subjects with vascular condition which interferes with ambulation
Known allergy or sensitivity to herbal products, soy or eggs
Vegetarian or Vegan
History or presence of cancer in the prior two years, except for non-melanoma skin cancer.
Individual has a condition the Investigator believes would interfere with his or her ability to provide informed consent, comply with the study protocol, which might confound the interpretation of the study results or put the person at undue risk
Untreated or unstable hypothyroidism, an active eating disorder, or evidence of any neurological disorders
Recent history of (within 12 months) or strong potential for alcohol or substance abuse
Pregnant, lactating, or unwilling to use adequate contraception during the study Subjects were required to undergo a 10 minute period of performance testing using a standardized stepmill test developed and validated by Medicus Research (Udani J K, unpublished observation). It involved exercising at level 4 on a StepMill® model 7000PT (StairMaster® Health & Fitness Products, Inc., Kirkland, Wash.) until one or both knees achieved a discomfort level of 5 on an 11 point (0-10) Likert scale [33]. This pain threshold had to be achieved within a 10 minute period otherwise the subject was excluded. Once the requisite pain level was achieved the subject was asked to continue stepping for an additional two minutes in order to record the maximum pain level achieved before disembarking from the stepmill. The following knee discomfort measures were recorded from the start of the stepmill test: (1) time to onset of initial joint pain; (2) time to onset of maximum joint pain; (3) time to initial improvement in knee joint pain; (4) time to 9 complete recovery from knee joint pain. Subjects who experienced a pain score of 5 (or greater) within one minute of starting the stress test were excluded. Out of 106 screened candidates, 55 subjects were enrolled in the study. Each subject voluntarily signed the IRB-approved informed consent form. After enrollment, the subjects were randomly assigned to either the placebo or the undenatured Type II collagen group.

Study Design and Trial Site

This randomized, double blind, placebo-controlled study was conducted at the Staywell Research clinical site located in Northridge, Calif. Medicus Research (Agoura Hills, Calif.) was the contract research organization (CRO) of record. The study protocol was approved by Copernicus Group IRB (Cary, N.C.) on Apr. 25, 2012. The study followed the principles outlined in the Declaration of Helsinki (version 1996).

Randomization and Blinding

Simple randomization was employed using a software algorithm based on the atmospheric noise method (www.random.org). Sequential assignment was used to determine group allocation. Once allocated, the assignment was documented and placed in individually numbered envelopes to maintain blinding. Subjects, clinical staff, plus data analysis and management staff remained blinded throughout the study.

Study Schedule

The study duration was 17 weeks with a total of 7 visits that included screening, baseline, days 7, 30, 60, 90 and 120 (final visit). Table 2 summarizes the study visits and activities. All subjects completed a medical history questionnaire at baseline and compliance reports during follow-up evaluations at 7, 30, 60, 90 and 120 days. Subjects were assessed for anthropometric measures, vital signs, knee range of motion (flexion and extension), six-minute timed walk, as well as the onset and recovery from pain using the Udani Stepmill Procedure. A Fitbit (San Francisco, Calif.) device was used to measure daily distance walked, steps taken and an average step length for study participants. Subjects were also asked to complete the KOOS survey as well as the Stanford exercise scales.

the first sign of pain in the target knee. The baselines at each time point were normalized to account for dropouts. Percent change in time to complete recovery from pain was measured as follows: a new stopwatch was started when the subjects disembarked from the stepmill and the time to complete recovery from pain was recorded. The baselines at each time point were normalized to account for dropouts then compared against the reference interval which was defined as the percentage change between the study baseline and day 7.

KOOS Knee Survey & Stanford Exercise Scales

The KOOS survey is a validated instrument consisting of 42 questions that are classified into sub-scales such as symptoms, stiffness, pain, daily activities, recreational activities and quality of life [34]. It measures the subjects' opinion about their knees and their ability to perform daily activities during the past week. The Stanford exercise behavior scale comprises 6 questions designed to assess exercise behaviors during the previous week [35].

TABLE 2

Protocol summary

| Protocol Activities | V1 Day-7 Screen | V2 Day 0 Baseline | V3 Day 7 | V4 Day 30 | V5 Day 60 | V6 Day 90 | V7 Day 120 End |
|---|---|---|---|---|---|---|---|
| Informed consent | x | | | | | | |
| Inclusion/Exclusion | x | | | | | | |
| Medical history and physical exam | x | | | | | | |
| Vital signs/anthropometric measures | x | x | x | x | x | x | x |
| Urine pregnancy test | x | x | | | | | |
| Administer and review scales/questionnaires/diaries | x | x | x | x | x | x | x |
| Stressor (Udani Stepmill protocol) | x | x | x | x | x | x | x |
| Functional measures (6-min timed walk) | x | x | x | x | x | x | x |
| Goniometry (range of motion) | | x | x | x | x | x | x |
| Review concomitant therapies | x | x | x | x | x | x | x |
| Intercurrent medical issues review | | x | x | x | x | x | x |
| Compliance assessment (including phone calls) | | x | x | x | x | x | x |
| Randomization | | x | | | | | |
| Study supplement preparation & dispensing | | | x | x | x | x | |

Knee Range of Motion Measurements

Knee extension was measured by goniometry. Briefly, subjects were instructed to sit in an upright position on a table edge with their backs straight (knee position defined as 90°). The axis of a goniometer was placed at the intersection of the thigh and shank at the knee joint. Subjects were asked to bring their knees to full extension without changing the position of the pelvis and lumbar spine. The extended knee joint angle was measured and recorded. For knee flexion measurement, subjects were asked to actively flex their knees while lying in a prone position with their shins off the end of the table. The range of knee flexion motion was then measured and documented.

Timed Joint Discomfort Measurements

Briefly, a stopwatch was started when subjects began climbing the stepmill. Time to onset of pain was recorded at Six Minute Timed Walk Subjects were instructed to walk up and down a hallway for 6 minutes as rapidly as possible without causing any pain. A measuring wheel (RoadRunner Wheel, Keson Industries, Aurora, Ill.) was used to measure distance travelled in 6 minutes.

Rescue Medication

No rescue medications were allowed during the course of the study. At all study visits, subjects were given a list of the 43 prohibited medications and supplements (Table 3). Changes in overall medication history, or the use of these substances, were then recorded by the study coordinator. Subjects found to have used any of these prohibited substances were excluded from further participation in the study as per protocol.

TABLE 3

Representative list of prohibited medications* by category

| Category | Medications |
|---|---|
| Joint supplements (Omega-3, Omega-6 plus others) | Alpha-Linolenic acid<br>Docosapentaenoic acid<br>Docosahexaenoic acid<br>Eicosatrienoic acid<br>Eicosatetraenoic acid<br>Eicosapentaenoic acid<br>Hexadecatrienoic acid<br>Heneicosapentaenoic acid<br>Stearidonic acid<br>Tetracosapentaenoic acid<br>Tetracosahexaenoic acid<br>Glucosamine (all forms)<br>Chondroitin (all forms)<br>Other herbal ingredients |
| NSAIDs (OTC and prescription) | Aspirin<br>Diflunisal<br>Diclofenac<br>Celecoxib<br>Etodolac<br>Fenoprofen<br>Flurbiprofen<br>Ibuprofen<br>Indomethacin<br>Ketoprofen<br>Meclofenamate<br>Mefenamic acid<br>Meloxicam<br>Nabumetone<br>Naproxen<br>Oxaprozin<br>Piroxicam<br>Rofecoxib<br>Sulindac<br>Tolmetin<br>Valdecoxib |

*Selected from a list of 43 prohibited medications and supplements

Statistics

Outcome variables were assessed for conformance to the normal distribution and transformed as required. Within group significance was analyzed by non-parametric Sign test or by non-parametric Wilcoxon Signed Rank test, while Wilcoxon Mann-Whitney test was used to analyze between groups significance. The Fisher Exact test was used to evaluate the complete loss of pain between study cohorts whereas the binomial test was used to assess the likelihood of complete loss of pain at each visit. P-values equal to or less than 0.05 were considered statistically significant. All analyses were done on a per protocol basis using SPSS, v19 (IBM, Armonk, N.Y.). Results were presented as mean±SEM.

Results

Baseline Demographics

A total of 55 individuals met the eligibility criteria and were randomized to the placebo (n=28) or to the undenatured Type II collagen (n=27) group. Baseline demographic characteristics for subjects in both groups were similar with respect to age, gender, height, weight and BMI (Table 4). A total of nine subjects, three in undenatured Type II collagen group and six in placebo group, were lost to follow-up. The results presented herein encompass 46 total subjects, 22 subjects in the placebo group plus 24 subjects in the undenatured Type II collagen group. It should be noted that the average age of the study participants was approximately 46 years which is about 16 years younger than the average age observed in many OA studies [36-38].

TABLE 4

Demographic and baseline characteristics of enrolled subjects

| Characteristics | UC-II | Placebo |
|---|---|---|
| Total number of subjects | 27 | 28 |
| Number of males | 11 | 12 |
| Number of females | 16 | 16 |
| Age (years) | 46.1 ± 1.5 | 46.6 ± 1.8 |
| Weight (kg) | 75.5 ± 2.9 | 77.5 ± 3.1 |
| Height (cm) | 167.1 ± 2.0 | 168.4 ± 2.0 |
| BMI (kg/m$^2$) | 26.8 ± 0.8 | 27.1 ± 0.7 |

Values are expressed as Mean ± SEM

Knee Extension and Flexion

FIG. 1 summarizes the average knee extension changes over time for subjects supplemented with either undenatured Type II collagen or placebo. The undenatured Type II collagen supplemented cohort presented with a statistically significant greater increase in the ability to extend the knee at day 120 as compared to the placebo group (81.0±1.3° vs 74.0±2.2°, p=0.011) and to baseline (81.0±1.3° vs 73.2±1.9°, p=0.002). The undenatured Type II collagen group 13 also demonstrated a significant increase in knee extension at day 90 (78.8±1.9° vs 73.2±1.9°, p=0.045) compared to baseline only. An intent to treat (ITT) analysis of these data also demonstrated a statistically significant net increase in knee extension at day 120 versus placebo (80.0±1.3° vs 73.7±1.8°, p=0.006). No statistically significant changes were observed in the placebo group at any time during this study. With respect to knee flexion, no significant changes were noted in either study group (p>0.05). The power associated with the former per protocol statistical analyses was 80%. Time to onset of initial joint pain is shown in FIG. 2. Supplementation with undenatured Type II collagen resulted in statistically significant increases in the time to onset of initial joint pain at day 90 (2.75±0.5 min, p=0.041) and at day 120 (2.8±0.5 min, p=0.019) versus a baseline of 1.4 min for each visit. No statistically significant differences were noted for either the placebo group or between groups Five individuals in the undenatured Type II collagen group and one in the placebo group reported no onset of pain by the end of study (see below and Table 5).

TABLE 5

Subjects reporting complete loss of knee pain on stepmill test

| Visit | UC-II No. of Pain Subjects (%) | UC-II Continuity pain lose | UC-II P value (Binomial | Placebo No. of Pain Subjects (%) | Placebo Continuity pain loss[#] | Placebo P value (Binomial |
|---|---|---|---|---|---|---|
| Baselin | 0.0 (0) | 0 | NA | 0.0 (0) | 0 | NA |
| Day 7 | 0.0 (0) | 0 | NA | 0.0 (0) | 0 | NA |
| Day 30 | 1.0 (4) | 1N | 0.5 | 0.0 (0) | 0 | NA |
| Day 60 | 3.0 (13) | 1R, 2N | 0.125 | 0.0 (0) | 0 | NA |
| Day 90 | 3.0 (13) | 2R, 1N | 0.125 | 1 (5) | 1N | 0.5 |
| Day | 5.0 (21) | 3R, 2N | 0.031[r] | 1 (5) | 1R | 0.5 |

Values denote number of subjects while parenthesis provides the percent of total subjects who did not have any pain on stepmill. Continuity indicates the number of subjects in whom the absence of pain was maintained across visits. *Significant at p≤0.05 based on independent binomial testing of each visit using the null hypothesis that the probability of a subject experiencing no joint pain is equal to zero. There was no statistical difference between groups. #R=Repeat subject (i.e. same subject who reported no pain in previous visit); N=New subject who reports no pain for the first time.

Given this unexpected finding, an additional analysis was undertaken which included these individuals in the time to onset of initial pain analysis. The 10 minute limit of the stepmill procedure was used as the lower limit to pain onset. Under these conservative assumptions, supplementation with undenatured Type II collagen yielded statistically significant increases in time to onset of pain at day 90 (3.65±0.7 min, p=0.011) and day 120 (4.31±0.7 min, p=0.002) versus a baseline of 1.4 min for each visit. The between-group comparison at day 120 approached the statistical level of significance favoring the undenatured Type II collagen cohort (p=0.051). 14 Time to onset of maximum joint pain A statistically significant difference between groups was noted at day 60 (6.39±0.5 min vs 4.78±0.5 min; p=0.025) favoring the undenatured Type II collagen cohort. This significance did not persist during the remainder of the study suggesting that this was a random occurrence.

Time to Initial Improvement in Knee Joint Pain.

The time to offset of joint pain was recorded immediately upon the subject stepping off the stepmill. Both groups began to recover from pain with the same rate resulting in no significant differences between groups in the time to initial offset of joint pain (p>0.05).

Time to Complete Recovery from Knee Joint Pain

The time to complete recovery from joint pain showed significant reductions at days 60, 90 and 120 compared to baseline for both the undenatured Type II collagen group as well as the placebo group (FIG. 3). Percent changes in times were calculated after normalizing the baselines against the reference range of baseline to day 7. The undenatured Type II collagen group exhibited average reductions of 31.9±11.7% (p=0.041), 51.1±6.1% (p=0.004) and 51.9±6.0% (p=0.011) at days 60, 90 and 120, respectively. By contrast, the reductions for the same time points for the placebo cohort, 21.9±10.2% (p=0.017), 22.2±15.5% (p=0.007) and 30.0±11.8% (p=0.012), were of lower magnitude but nonetheless statistically significant versus baseline. None of these between group differences achieved statistical significance.

Time to Complete Loss of Knee Joint Pain

During the course of this study it was noted that a number of subjects in both the placebo and the supplemented cohorts no longer reported any pain during the 15 stepmill protocol. For the undenatured Type II collagen group, 5 subjects (21%) no longer reported pain by day 120, whereas only 1 subject (5%) in placebo group reported complete loss of pain (Table 4). This effect did not reach statistical significance between groups but there was an evident trend in the data towards a greater number of subjects losing pain in the undenatured Type II collagen cohort (p=0.126). A binomial analysis for complete loss of pain at each visit demonstrated a statistical significance for the undenatured Type II collagen group by day 120 (p=0.031). It is important to note that the complete loss of knee pain was not a random event. The pattern among the subjects indicates that loss of knee pain appeared to be a persistent phenomenon that spanned multiple visits (Table 4).

A detailed review of the clinical report forms showed that none of these individuals consumed pain relief medication prior to their visits.

Six-Minute Timed Walk & Daily Number of Steps

No significant differences were observed between the study groups for the six-minute time walk or the daily number of steps taken (p>0.05). The distance walked in six-minutes by the undenatured Type II collagen (range=505 to 522 meters) and the placebo (range=461 to 502 meters) groups were within the reference range previously reported [39] for healthy adults (399 to 778 meters, males; 310 to 664 meters, females). Similarly, the average step length calculated from Fitbit data for both study groups (0.69 to 0.71 meters) also agreed with previously published results for normal adults [40].

KOOS Knee Survey & Stanford Exercise Scales

No significant differences were seen between the study groups for either the KOOS survey or the Stanford exercise scale (p>0.05).

Use of Analgesics and NSAIDs

Review of the clinical report forms showed that no subject in either study cohort consumed any of the 43 prohibited medicines or supplements during the study.

Safety Assessments

A total of eight adverse events equally dispersed between both groups were noted (Table 6). None of the adverse events was considered to be associated with undenatured Type II collagen supplementation. All events resolved spontaneously without the need for further intervention. No subject withdrew from the study due to an adverse event. Finally, no differences were observed in vital signs after seventeen weeks of supplementation, and no serious adverse events were reported in this study.

TABLE 6

Summary of analysis of adverse events (AEs) in all subjects

| Study groups | Adverse event (Body system) | Number of AEs |
|---|---|---|
| UC-II | Upper respiratory infection (Pulmonary) | 3 |
| UC-II | Food Poisoning (Gastrointestinal) | 1 |
| Total number of AEs | | 4 |
| Total number of subjects reporting AEs: n | | 4/27 |
| Placebo | Bilateral ankle edema (Musculoskeletal) | 1 |
| Placebo | Right ankle fracture (Musculoskeletal) | 1 |
| Placebo | Sinusitis (Ears/Nose/Throat) | 1 |
| Placebo | Skin infection right ankle (Dermatological) | 1 |
| Total number of AEs | | 4 |
| Total number of subjects reporting AEs: n | | 2/28 |

Discussion

At study conclusion, it was found that subjects ingesting the undenatured Type II collagen supplement experienced a significantly greater forward range of motion (ROM) in their knees versus baseline and placebo as measured by knee extension goniometry. Knee extension is necessary for daily function and sport activities. Loss of knee extension has been shown to negatively impact the function of the lower extremity [42, 43]. For example, loss of knee extension can cause altered gait patterns affecting ankles and the hip which could result in difficulty with running and jumping [42, 43]. Studies have further shown that a permanent loss of 3-5° of extension can significantly impact patient satisfaction and the development of early arthritis [44].

From a structure-function perspective this outcome is not surprising. During the earliest characterized phases of OA there is an apparent preferential loss of knee extension over knee flexion, and this loss has been shown to correlate with WOMAC pain scores [45, 46]. In addition, MRI imaging of the early osteoarthritic knee has shown that initial changes in knee structure appear to center on articular cartilage erosions (fibrillations) about the patella and other weight bearing regions of the knee [47]. Such changes might favor a loss in knee ROM that preferentially affects extension over flexion. The pathophysiology of the early osteoarthritic knee, it is believed, provides insight regarding the effect of daily physical activities on the healthy knee insofar as it helps explain the discordance in clinical outcomes between knee extension and flexion.

Both the time to onset of initial joint pain as well as full recovery from it were measured in this study. For each of these measures the clinical outcomes favored the undenatured Type II collagen supplemented cohort versus their baseline status. The ability of undenatured Type II collagen to modulate knee extension may relate to its ability to moderate knee joint pain. Crowley et al. [26] and Trentham et al. [25] demonstrated that undenatured Type II collagen effectively enhances joint comfort and flexibility thereby improving the quality of life (QoL) in both OA and RA subjects, respectively. This effect may be attributable to the finding that microgram quantities of undenatured type II collagen moderate CIA in both the rat and the mouse via the induction of T regulator cells [27, 28, 48]. The induction of these T regulators takes place within gut associated lymphatic tissues (GALT), including mesenteric lymph nodes, in response to the consumption of undenatured type II collagen [27]. Studies have shown that these regulatory cells produce IL-10 and TGF-$\beta$ [30, 49]. A special class of CD103+ dendritic cells, found almost exclusively in the GALT, facilitates this process [48, 50]. Once activated, T regulator cells appear to down-regulate a wide range of immunologic and proinflammatory activities resulting in the moderation of the arthritic response initiated by undenatured type II collagen [27]. The phenomenon of oral tolerance has also been demonstrated in humans, and appears to involve a similar set of T regulators [30, 51-53].

The above description of how undenatured Type II collagen might modulate joint function is most easily understood in the context of RA given that the CIA animal model resembles this disease most closely [27, 28, 54]. However, the case for T regulators and immune cytokines having a moderating effect on healthy or OA knee joint function appears less apparent. This view has changed in recent years due to a growing body of evidence suggesting that both OA and normal chondrocyte biology appears to be regulated by some of the same cytokines and chemokines that regulate inflammation [5, 6, 55]. For example, Mannelli and coworkers [56] recently reported that feeding microgram amounts of native type II collagen (porcine) prevents monoiodoacetate-induced articular cartilage damage in this rat model of 19 osteoarthritis, as measured by pain thresholds and by circulating levels of cross linked c-telopeptides derived from type II collagen. This finding corroborates the efficacy of undenatured type II collagen in improving joint comfort in osteoarthritic conditions [26].

In the present study, it is shown that undenatured Type II collagen can improve joint function in healthy subjects undergoing strenuous physical exercise. This observation, when considered in context with normal chondrocyte physiology, suggests that activated T regulator cells, specific for undenatured type II collagen, home to an overstressed knee joint where their release of the anti-inflammatory cytokines, IL-10 and TGF-$\beta$ reverse the catabolic changes caused by strenuous exertion [13, 21, 57]. In addition, the IL-10 and TGF-$\beta$ produced by these T regulators may tilt the T H balance in the knee joint towards T H 2 [30, 58] responses which preferentially result in IL-4 production further fostering a shift in chondrocyte metabolism towards ECM replenishment.

Several additional tests were used in this study to assess overall joint function, quality of life, and physical activity. The additional parameters and tests measured included a six minute timed walk plus the Stanford exercise scale and KOOS survey. With respect to the KOOS survey, both cohorts were statistically significant versus baseline for symptoms, pain, daily function, recreational activities and quality of life but were not significant from each other. This was not an unexpected finding given that this study was carried out with healthy subjects who do not present with any joint issues at rest. It is only when the knee is stressed via the stepmill that subjects report any joint discomfort. Under these conditions, and as indicated above, the undenatured Type II collagen group appears to experience less joint discomfort and greater joint flexibility.

No difference in clinical outcomes between groups was seen in the six minute timed walk, the daily distance walked, or the Stanford exercise scale questionnaire. Once again this result was not surprising given that these tests and questionnaires are designed and clinically validated to assess the severity of arthritic disease in unhealthy populations.

No clinical biomarkers associated with arthritic diseases were assessed in this study. Healthy subjects would not be expected to present with significant alterations in their inflammatory biomarker profile as they lack clinical disease [59]. In addition, it should be noted that the joint discomfort measured in this study is acute pain induced by a stressor rather than due to an ongoing inflammatory event. Therefore, any elevation in inflammation markers that might occur in these healthy subjects may simply be due to the physiological impact of strenuous exercise.

There are two study limitations to consider when reviewing these results. The first, time to onset of initial pain, was limited to a 10-minute interval. The current study design did not address the possibility that subjects might cease to experience pain on the stepmill. Future studies should allow for an extension of the exertion interval in order to gauge how much longer a subject can exercise before reporting pain. In this way better defined parameters can be placed upon the degree to which undenatured Type II collagen supplementation results in the cessation of joint pain due to strenuous exercise in healthy subjects.

The second limitation that merits consideration is the possibility that study subjects may have early signs of arthritis that do not meet the ACR criteria. This possible limitation was addressed by performing an extensive medical examination 21 for signs and symptoms of OA and by excluding volunteers who experienced pain levels of 5 or greater within one minute of using the stepmill.

UC-II® brand undenatured Type II collagen is a unique ingredient that supports healthy joints. Previous studies have focused on the efficacy of this ingredient in OA subjects. By including healthy subjects in this study, and using non-disease endpoints as a measure of efficacy, it is believed that the benefits that derive from undenatured Type II collagen usage now extends to include healthy individuals. Further, this ingredient appears to be safe for human consumption based on an extensive series of in vivo and in vitro toxicological studies as well as the absence of any adverse events in this and in previous human studies [24, 26, 60]. In conclusion, daily supplementation with 40 mg of UC-II brand undenatured Type II collagen supports joint function and flexibility in healthy subjects as demonstrated by greater knee extension and has the potential both to alleviate the joint pain that occasionally arises from strenuous exercise as well as to lengthen periods of pain free exertion.

Fifty-five subjects, who reported knee pain after participating in a standardized stepmill performance test, were randomized to the placebo (n=28) or the UC-II® brand undenatured Type II collagen (40 mg daily, n=27 cohort for 120 days. Joint function was assessed by measuring knee flexion and knee extension as well as time to experiencing and recovering from joint pain following strenuous stepmill exertion.

After 120 days of supplementation, subjects in the group receiving undenatured Type II collagen exhibited a statistically significant improvement in average knee extension compared to placebo (81.0±1.3° vs 74.0±2.2°; p=0.011) and to baseline (81.0±1.3° vs 73.2±1.9°; p=0.002). The undenatured Type II collagen cohort also demonstrated a statistically significant change in average knee extension at day 90 (78.8±1.9° vs 73.2±1.9°; p=0.045) versus baseline. No significant change in knee extension was observed in the placebo group at any time. It was also noted that the undenatured Type II collagen group exercised longer before experiencing any initial joint discomfort at day 120 (2.8±0.5 min, p=0.019), compared to baseline (1.4±0.2 min). By contrast, no significant changes were seen in the placebo group. No product related adverse events were observed during the study. At study conclusion, five individuals in the undenatured Type II collagen cohort reported no pain during or after the stepmill protocol (p=0.031, within visit) as compared to one subject in the placebo group.

Accordingly it is concluded that daily supplementation with 40 mg of UC-II® brand undenatured Type II collagen containing 10.4±1.3 mg of native type-II collagen was well tolerated and led to improved knee joint extension in healthy subjects. UC-II also demonstrated the potential to lengthen the period of pain free strenuous exertion and alleviate the joint pain that occasionally arises from such activities.

Numerous modifications and variations in the practice of the invention are expected to occur to those skilled in the art upon consideration of the presently preferred embodiments thereof. Consequently, the only limitations which should be placed upon the scope of the invention are those which appear in the appended claims.

Abbreviations

RA=rheumatoid arthritis; OA=osteoarthritis; ECM=extracellular matrix; TNF-α=tumor necrosis factor-alpha; IL-1β=interleukin-1 beta; IL-6=interleukin-6; IL-4=interleukin 4; IL-10=interleukin-10; MMP=matrix metalloproteinase; NF-κB=nuclear factor-kappa-light-chain-enhancer of activated B cells; MAPK=mitogen activated protein kinase; ERK=extracellular receptor kinase; NO=nitric oxide; TGF-β=transforming growth factor-beta; CIA=collagen induced arthritis; KOOS=knee injury and osteoarthritis outcome score; ROM=range of motion; MRI=magnetic resonance imaging; GALT=gut associated lymphatic tissue; QoL=quality of life; MIP-1β=macrophage inflammatory protein-1 beta; IP-10=interferon gamma-induced protein 10; T H=T helper cell; WOMAC=western Ontario and McMaster universities osteoarthritis index; ACR=American College of Rheumatology.

REFERENCES

1. Shek P N and Shephard R J: Physical exercise as a human model of limited inflammatory response. Can J Physiol Pharmacol 1998, 76:589-97.
2. Kiviranta I, Tammi M, Jurvelin J, et al.: Articular cartilage thickness and glycosaminoglycan distribution in the canine knee joint after strenuous running exercise. Clin Orthop Relat Res 1992:302-8.
3. Guilak F: Biomechanical factors in osteoarthritis. Best Pract Res Clin Rheumatol 2011, 25:815-23.
4. Kawamura S, Lotito K, and Rodeo S A: Biomechanics and healing response of the meniscus. Oper Tech Sports Med 2003, 11:68-76.
5. Ramage L, Nuki G, and Salter D M: Signalling cascades in mechanotransduction: Cell-matrix interactions and mechanical loading. Scand J Med Sci Sports 2009, 19:457-69.
6. Honda K, Ohno S, Tanimoto K, et al.: The effects of high magnitude cyclic tensile load on cartilage matrix metabolism in cultured chondrocytes. Eur J Cell Biol 2000, 79:601-9.
7. Agarwal S, Deschner J, Long P, et al.: Role of NF-kappab transcription factors in antiinflammatory and proinflammatory actions of mechanical signals. Arthritis Rheum 2004, 50:3541-8. 25
8. Berg V, Sveinbjornsson B, Bendiksen S, et al.: Human articular chondrocytes express chemR23 and chemerin; chemR23 promotes inflammatory signalling upon binding the ligand chemerin (21-157). Arthritis Res Ther 2010, 12:R228.
9. Millward-Sadler S J, Wright M O, Lee H, et al.: Integrin-regulated secretion of interleukin 4: A novel pathway of mechanotransduction in human articular chondrocytes. J Cell Biol 1999, 145:183-9.
10. Millward-Sadler S J, Wright M O, Davies L W, et al.: Mechanotransduction via integrins and interleukin-4 results in altered aggrecan and matrix metalloproteinase 3 gene expression in normal, but not osteoarthritic, human articular chondrocytes. Arthritis Rheum 2000, 43:2091-9.
11. Doi H, Nishida K, Yorimitsu M, et al.: Interleukin-4 downregulates the cyclic tensile stress-induced matrix metalloproteinases-13 and cathepsin b expression by rat normal chondrocytes. Acta Med Okayama 2008, 62:119-26.
12. Yorimitsu M, Nishida K, Shimizu A, et al.: Intra-articular injection of interleukin-4 decreases nitric oxide production by chondrocytes and ameliorates subsequent destruction of cartilage in instability-induced osteoarthritis in rat knee joints. Osteoarthritis Cartilage 2008, 16:764-71.
13. van Meegeren M E, Roosendaal G, Jansen N W, et al.: IL-4 alone and in combination with IL-10 protects against blood-induced cartilage damage. Osteoarthritis Cartilage 2012, 20:764-72. 26
14. Pufe T, Lemke A, Kurz B, et al.: Mechanical overload induces VEGF in cartilage discs via hypoxia-inducible factor. Am J Pathol 2004, 164:185-92.
15. Ostrowski K, Rohde T, Asp S, et al.: Pro- and anti-inflammatory cytokine balance in strenuous exercise in humans. J Physiol 1999, 515 (Pt 1):287-91.
16. Allen J L, Cooke M E, and Alliston T: ECM stiffness primes the TGFbeta pathway to promote chondrocyte differentiation. Mol Biol Cell 2012, 23:3731-42.
17. Bougault C, Aubert-Foucher E, Paumier A, et al.: Dynamic compression of chondrocyte-agarose constructs reveals new candidate mechanosensitive genes. PLoS One 2012, 7:e36964.
18. Li T F, O'Keefe R J, and Chen D: TGF-beta signaling in chondrocytes. Front Biosci 2005, 10:681-8.

19. Donovan J and Slingerland J: Transforming growth factor-beta and breast cancer: Cell cycle arrest by transforming growth factor-beta and its disruption in cancer. Breast Cancer Res 2000, 2:116-24.
20. Rosier R N, O'Keefe R J, Crabb I D, et al.: Transforming growth factor beta: An autocrine regulator of chondrocytes. Connect Tissue Res 1989, 20:295-301.
21. Roman-Blas J A, Stokes D G, and Jimenez S A: Modulation of TGF-beta signaling by proinflammatory cytokines in articular chondrocytes. Osteoarthritis Cartilage 2007, 15:1367-77. 27
22. Loeser R F: Aging and osteoarthritis: The role of chondrocyte senescence and aging changes in the cartilage matrix. Osteoarthritis Cartilage 2009, 17:971-9.
23. van Beuningen H M, van der Kraan P M, Arntz O J, et al.: Protection from interleukin 1 induced destruction of articular cartilage by transforming growth factor beta: tudies in anatomically intact cartilage in vitro and in vivo. Ann Rheum Dis 1993, 52:185-91.
24. Bagchi D, Misner B, Bagchi M, et al.: Effects of orally administered undenatured type II collagen against arthritic inflammatory diseases: A mechanistic exploration. Int J Clin Pharmacol Res 2002, 22:101-10.
25. Trentham D E, Dynesius-Trentham R A, Orav E J, et al.: Effects of oral administration of type II collagen on rheumatoid arthritis. Science 1993, 261:1727-30.
26. Crowley D C, Lau F C, Sharma P, et al.: Safety and efficacy of undenatured type II collagen in the treatment of osteoarthritis of the knee: A clinical trial. Int J Med Sci 2009, 6:312-21.
27. Tong T, Zhao W, Wu Y Q, et al.: Chicken type II collagen induced immune balance of main subtype of helper T cells in mesenteric lymph node lymphocytes in rats with collagen-induced arthritis. Inflamm Res 2010, 59:369-77.
28. Nagler-Anderson C, Bober L A, Robinson M E, et al.: Suppression of type II collagen-induced arthritis by intragastric administration of soluble type II collagen. Proc Natl Acad Sci USA 1986, 83:7443-6. 28
29. Brandtzaeg P: 'ABC' of mucosal immunology. Nestle Nutr Workshop Ser Pediatr Program 2009, 64:23-38; discussion 38-43, 251-7.
30. Weiner H L, da Cunha A P, Quintana F, et al.: Oral tolerance. Immunol Rev 2011, 241:241-59.
31. Aletaha D, Neogi T, Silman A J, et al.: 2010 rheumatoid arthritis classification criteria: An american college of rheumatology/european league against rheumatism collaborative initiative. Arthritis Rheum 2010, 62:2569-81.
32. Altman R, Asch E, Bloch D, et al.: Development of criteria for the classification and reporting of osteoarthritis. Classification of osteoarthritis of the knee. Diagnostic and therapeutic criteria committee of the american rheumatism association. Arthritis Rheum 1986, 29:1039-49.
33. Likert R: A technique for the measurement of attitudes. Arch Psychol 1932, 22:1-55.
34. Roos E M, Roos H P, Ekdahl C, et al.: Knee injury and osteoarthritis outcome score (KOOS)—validation of a swedish version. Scand J Med Sci Sports 1998, 8:439-48.
35. Lorig K, Stewart A, Ritter P, et al.: Outcome measures for health education and other health care interventions. Outcome measures for health education and other health care interventions. Thousand Oaks, Calif.: SAGE Publications, Inc.; 1996.
36. Hawkey C, Laine L, Simon T, et al.: Comparison of the effect of rofecoxib (a cyclooxygenase 2 inhibitor), ibuprofen, and placebo on the gastroduodenal mucosa of patients with osteoarthritis: A randomized, double-blind, placebo-controlled trial. The rofecoxib osteoarthritis endoscopy multinational study group. Arthritis Rheum 2000, 43:370-7.
37. Pincus T, Koch G G, Sokka T, et al.: A randomized, double-blind, rossover clinical trial of diclofenac plus misoprostol versus acetaminophen in patients with osteoarthritis of the hip or knee. Arthritis Rheum 2001, 44:1587-98.
38. Petrella R J, DiSilvestro M D, and Hildebrand C: Effects of hyaluronate sodium on pain and physical functioning in osteoarthritis of the knee: A randomized, double-blind, placebo-controlled clinical trial. Arch Intern Med 2002, 162:292-8.
39. Enright P L and Sherrill D L: Reference equations for the six-minute walk in healthy adults. Am J Respir Crit Care Med 1998, 158:1384-7.
40. Perry J: Gait analysis: Normal and pathological function. Thorofare: SLACK Inc.; 1992.
41. Viera A J: Predisease: When does it make sense? Epidemiol Rev 2011, 33:122-34.
42. Norkin C C and Levangie P K: Joint structure & function: A comprehensive analysis Philadelphia: F. A. Davis; 1992.
43. Shah N: Increasing knee range of motion using a unique sustained method. N Am J Sports Phys Ther 2008, 3:110-3.
44. Shelbourne K D, Biggs A, and Gray T: Deconditioned knee: The effectiveness of a rehabilitation program that restores normal knee motion to improve symptoms and function. N Am J Sports Phys Ther 2007, 2:81-9. 30
45. Serrao P R, Gramani-Say K, Lessi G C, et al.: Knee extensor torque of men with early degrees of osteoarthritis is associated with pain, stiffness and function. Rev Bras Fisioter 2012, 16:289-94.
46. Heiden T L, Lloyd D G, and Ackland T R: Knee extension and flexion weakness in people with knee osteoarthritis: Is antagonist cocontraction a factor? J Orthop Sports Phys Ther 2009, 39:807-15.
47. Karantanas A H, Magnetic resonance imaging findings in early osteoarthritis of the knee, in Touch Brief. 2007. p. 37-40.
48. Park M J, Park K S, Park H S, et al.: A distinct tolerogenic subset of splenic IDO(+)CD11b(+) dendritic cells from orally tolerized mice is responsible for induction of systemic immune tolerance and suppression of collagen-induced arthritis. Cell Immunol 2012, 278:45-54.
49. Li M O and Flavell R A: TGF-beta: A master of all T cell trades. Cell 2008, 134:392-404.
50. Coombes J L, Siddiqui K R, Arancibia-Carcamo C V, et al.: A functionally specialized population of mucosal CD103+ dcs induces Foxp3+ regulatory t cells via a TGF-beta and retinoic acid-dependent mechanism. J Exp Med 2007, 204:1757-64.
51. Ban Y, Zigmond E, Lalazar G, et al.: Oral administration of OKT3 monoclonal antibody to human subjects induces a dose-dependent immunologic effect in T cells and dendritic cells. J Clin Immunol 2010, 30:167-77. 31
52. Caminiti L, Passalacqua G, Barberi S, et al.: A new protocol for specific oral tolerance induction in children with ige-mediated cow's milk allergy. Allergy Asthma Proc 2009, 30:443-8.
53. Ben Ahmed M, Belhadj Hmida N, Moes N, et al.: IL-15 renders conventional lymphocytes resistant to suppressive functions of regulatory T cells through activation of the phosphatidylinositol 3-kinase pathway. J Immunol 2009, 182:6763-70.
54. Courtenay J S, Dallman M J, Dayan A D, et al.: Immunisation against heterologous type II collagen induces arthritis in mice. Nature 1980, 283:666-8.

55. Pelletier J P, Martel-Pelletier J, and Abramson S B: Osteoarthritis, an inflammatory disease: Potential implication for the selection of new therapeutic targets. Arthritis Rheum 2001, 44:1237-47.
56. Di Cesare Mannelli L, Micheli L, Zanardelli M, et al.: Low dose native type II collagen prevents pain in a rat osteoarthritis model. BMC Musculoskelet Disord 2013, 14:228.
57. Muller R D, John T, Kohl B, et al.: IL-10 overexpression differentially affects cartilage matrix gene expression in response to TNF-alpha in human articular chondrocytes in vitro. Cytokine 2008, 44:377-85.
58. Zouali M: Immunological tolerance: Mechanisms. eLS: John Wiley & Sons, Ltd; 2001. 32
59. Chu C R, Williams A A, Coyle C H, et al.: Early diagnosis to enable early treatment of pre-osteoarthritis. Arthritis Res Ther 2012, 14:212.
60. Marone P A, Lau F C, Gupta R C, et al.: Safety and toxicological evaluation of undenatured type ii collagen. Toxicol Mech Methods 2010, 20:175-89.

What is claimed is:

1. A method of treating exercise-induced joint pain in an arthritis-free mammal comprising administering undenatured Type II collagen in an amount effective to reduce such exercise-induced joint pain, wherein the reduction in joint pain is evidenced by improvements in range motion.

2. A method of lengthening the period of joint pain free strenuous exercise in an arthritis-free mammal comprising administering undenatured Type II collagen in an amount effective to lengthen the period of strenuous exercise before joint pain is experienced, wherein the reduction in joint pain is evidenced by improvements in range motion.

3. A method of speeding recovery from exercise-induced joint pain in arthritis-free mammals comprising administering undenatured Type II collagen in an amount effective to speed the recovery from exercise-induced joint pain, wherein the reduction in joint pain is evidenced by improvements in range motion.

4. A method of treating joint pain in an arthritis-free mammal which is due to a mechanical stressor comprising administering undenatured Type II collagen in an amount effective to reduce such joint pain, wherein the reduction in joint pain is evidenced by improvements in range motion.

5. The method of claim 4 wherein the mechanical stressor is acute injury.

6. The method of claim 4 wherein the mechanical stressor is strenuous exercise.

7. A method of reducing joint pain during strenuous exercise in arthritis-free mammals comprising administering undenatured Type II collagen in an amount effective to reduce such exercise-induced joint pain wherein the joint pain is knee pain and wherein the reduction in knee joint pain is evidenced by improvements in range of motion.

8. A method of reducing joint pain during strenuous exercise in arthritis-free mammals comprising administering undenatured Type II collagen in an amount effective to reduce such exercise-induced joint pain wherein the joint pain is knee pain and wherein the reduction in knee joint pain is evidenced by improvements in knee joint extension.

9. The method of claim 7 or 8 wherein the mammal is a human.

10. The method of claim 7 or 8 wherein the undenatured Type II collagen is administered in a dosage of from 0.1 mg to 5000 mg per day.

11. The method of claim 7 or 8 wherein the undenatured Type II collagen is administered in a dosage of from 1 mg to 200 mg per day.

12. The method of claim 7 or 8 wherein the undenatured Type II collagen is administered in a dosage of from 5 mg to 40 mg per day.

13. The method of claim 7 or 8 wherein the undenatured Type II collagen is consumed orally.

14. The method of claim 7 or 8 wherein the undenatured Type II collagen is consumed in the form of a dosage form selected from the group consisting of capsules, tablets, gummy chewable, lozenge, powder.

15. The method of claim 7 or 8 wherein the undenatured Type II collagen is consumed in a syrup or liquid suspension.

16. The method of claim 7 or 8 wherein the undenatured Type II collagen is consumed in the form of an edible supplement.

* * * * *

UNITED STATES PATENT AND TRADEMARK OFFICE
CERTIFICATE OF CORRECTION

| | | |
|---|---|---|
| PATENT NO. | : 9,066,926 B2 | Page 1 of 1 |
| APPLICATION NO. | : 14/153841 | |
| DATED | : June 30, 2015 | |
| INVENTOR(S) | : Paul Dijkstra et al. | |

It is certified that error appears in the above-identified patent and that said Letters Patent is hereby corrected as shown below:

On the Title Page:

At item (56), on Page 2, under "OTHER PUBLICATIONS", in Column 1, line 23, delete "steoarthritis" and insert -- osteoarthritis --, therefor.

In the Specification:

At Column 20, line 52, "Ban Y," should be -- Ilan Y, --.

In the Claims:

At Column 21, line 26, "motion." should be -- of motion. --.

At Column 21, line 32, "motion." should be -- of motion. --.

At Column 21, line 38, "motion." should be -- of motion. --.

At Column 22, line 2, "motion." should be -- of motion. --.

Signed and Sealed this
Thirtieth Day of August, 2016

Michelle K. Lee
*Director of the United States Patent and Trademark Office*